| United States Patent [19] | [11] Patent Number: 4,840,955 |
|---|---|
| Sircar | [45] Date of Patent: Jun. 20, 1989 |

[54] 6-SUBSTITUTED-2(1H)-QUINOLINONES AND RELATED COMPOUNDS HAVING USE AS CARDIOTONIC, ANTIHYPERTENSIVE, AND ANTITHROMBOTIC AGENTS

[75] Inventor: Ila Sircar, Ann Arbor, Mich.

[73] Assignee: Warner-Lambert Company, Morris Plains, N.J.

[21] Appl. No.: 87,570

[22] Filed: Aug. 20, 1987

Related U.S. Application Data

[63] Continuation of Ser. No. 846,410, Mar. 31, 1986, abandoned, which is a continuation of Ser. No. 685,639, Dec. 24, 1984, abandoned.

[51] Int. Cl.$^4$ .................. C07D 401/04; C07D 403/04; A61K 31/47; A61K 31/415
[52] U.S. Cl. ..................................... 514/278; 546/15; 546/157; 546/158; 548/336; 548/364; 548/486; 514/312; 514/404
[58] Field of Search ...................... 514/312, 404, 278; 546/157, 158, 15; 548/364

[56] References Cited

U.S. PATENT DOCUMENTS

| 4,258,185 | 3/1981 | Nakao et al. | 546/157 |
|---|---|---|---|
| 4,526,982 | 7/1985 | Morrison | 544/371 |
| 4,550,119 | 10/1985 | Morrison | 514/394 |
| 4,591,591 | 5/1986 | Robertson | 514/254 |
| 4,661,484 | 12/1984 | Okushima et al. | 514/248 |
| 4,717,730 | 1/1988 | Sircar et al. | 514/252 |

FOREIGN PATENT DOCUMENTS

| 126651 | 11/1984 | European Pat. Off. . |
|---|---|---|
| 1466547 | 3/1977 | United Kingdom . |
| 2031404 | 4/1980 | United Kingdom . |

*Primary Examiner*—Anton H. Sutto
*Assistant Examiner*—E. Bernhardt
*Attorney, Agent, or Firm*—Joan Thierstein

[57] ABSTRACT

Novel 6-substituted-2(1H)-quinoline and related compounds having usefulness as cardiotonic, antihypertensive, and antithrombotic (platelet aggregation inhibition) agents.

8 Claims, No Drawings

6-SUBSTITUTED-2(1H)-QUINOLINONES AND RELATED COMPOUNDS HAVING USE AS CARDIOTONIC, ANTIHYPERTENSIVE, AND ANTITHROMBOTIC AGENTS

This is a continuation of U.S. Ser. No. 846,410 filed Mar. 31, 1986 abandoned which is a continuation of U.S. Ser. No. 685,639 filed Dec. 24, 1984 abandoned.

BACKGROUND OF THE INVENTION

The present invention relates to 6-substituted-2(1H)-quinolinone and related compounds having usefulness for the treatment of congestive heart failure and the therapy of thromboembolic diseases.

Cardiotonic agents having the structure XXX are disclosed in U.S. application Ser. No. 497,316 now U.S. Pat. No. 4,526,982 issued July 2, 1985. However, such agents of formula XXX do not make the novel quinolinones of the present invention obvious. Additionally, compounds of formula XX may be found in British Pat. No. 2,031,404 having antithrombotic and antihypertensive use. Again the combination of cyclic groups in the present invention is not taught.

SUMMARY OF THE INVENTION

The present invention relates to novel 6-substituted-2(1H)-quinolinone and related compounds useful as cardiotonic, antihypertensive, and antithrombotic agents having the structural formula I wherein X is $(CH_2)_n$ wherein n is 1 or 2, or $CR_4=CR_5$ wherein $R_4$ and $R_5$ are independently hydrogen or lower alkyl; R and $R_1$ are independently hydrogen, lower alkyl, or aralkyl; $R_2$ and $R_3$ are independently lower alkyl or $R_2$ and $R_3$ are taken together with the carbon to which each is attached to form a ring containing three to six carbons, inclusive.

Lower alkyl in the present invention means alkyl of from one to six carbons, inclusive. Aralkyl means optionally substituted phenyl attached through an alkyl of from one to three carbons, inclusive. The substituted phenyl includes one to three substituents such as alkyl of from one to six carbons, inclusive, alkoxy of from one to six carbons, inclusive, hydroxy, halogen, and the like. Halogen herein may be particularly chloro, fluoro, bromo, trifluoromethyl, and iodo, but preferably fluoro, trifluoromethyl, or chloro, the alkyl or alkoxy may be straight or branched hydrocarbons.

The present invention further relates to a method for treating congestive heart failure, hypertension, or diseases advantageously treated with platelet aggregation inhibitors such as thromboembolism in a patient which comprises administering orally or parenterally in a solid or liquid dosage form to such patient an effective amount of compounds having the structure I as defined above. The method of treatment increases cardiac contractility, decreases hypertension, and inhibits platelet aggregation in a patient requiring such treatment.

Another aspect of the present invention relates to a pharmaceutical composition for increasing cardiac contractility for lowering blood pressure or for inhibiting platelet aggregation, said composition comprising an effective amount of a compound of formula I as defined above and a pharmaceutically acceptable carrier.

The process for producing the quinolinone compounds of formula I comprises reacting an appropriately substituted quinolinone having the formula II wherein X, R, $R_2$, and $R_3$ are as defined above and Alk is alkyl of from one to four carbon atoms, and preferably methyl or ethyl, with $R_1NHNH_2$ wherein $R_1$ is as defined above. The reaction temperature is preferably at the boiling point of the solvent, that for example, may be an alcohol such as methanol or ethanol. See Scheme I.

The preparation of a compound for formula II is generally accomplished as shown in Scheme II. 6-Acetyl-3,4-dihydro-1-methyl-2(1H)-quinolinone of formula IV or appropriate compound having the desired X may be used as a starting material. The starting material is prepared by following the procedure described in Japan. Kokai 76,115,480 (Chem. Abs. 86, 121190W, 1977). Steps I and II of Scheme II are generally within ranges of reaction parameters determined by skill in the art from those shown as Preparations I and II respectively, hereinafter. The alkylation step II for a compound of formula I where R is lower alkyl may precede step I or be omitted as determined by convenience and desired end product.

The alkylation step shown as step II in Scheme II may be accomplished in one step or in a step-wise manner depending on whether $R_2$ and $R_3$ are the same or different. That is, the appropriate alkyl ester of β-oxobezenepropionic acid is reacted with lower alkyl halide; such as iodide, chloride, or bromide, in the presence of sodium hydride in a polar aprotic solvent, such as dimethylformamide. The preferred halide is iodide.

The compounds of formula II wherein R, $R_1$, and $R_2$ are different can also be prepared from compounds of formula IV by following steps shown in scheme III.

The reaction conditions of Scheme II or III are within the ordinary skill of the art.

Preferred compounds of the present invention include compounds of formula I wherein X is $(CH_2)_2$. Also preferred are compounds of formula I wherein R, $R_2$, and $R_3$ are methyl.

A particularly preferred compound of the present invention is 6-(4,5-dihydro-4,4-dimethyl-5-oxo-1H-pyrazol-3-yl)3,4-dihydro-1-methyl-2(1H)-quinolinone.

The compounds of formula I where $R_1$ is hydrogen may exist in tautomeric form; for example as illustrated by $I^1 \rightleftarrows I^2$. Also covered in the invention are tautomeric forms where R is hydrogen and X is $CR_4=CR_5$ as shown by $I^3 \rightleftarrows I^4$.

The following Examples will further illustrate the invention without, however, limiting it thereto.

PREPARATION 1

1,2,3,4-Tetrahydro-1-methyl-β,2-dioxo-6-quinolinepropanoic acid, methyl ester (III)

To a slurry of 1.6 g of NaH (60% dispersion in Nujol; 0.036 mol) in 10 ml of of THF is added dropwise with stirring a solution of 2.3 g (0.012 mol) of 6-acetyl-3,4-dihydro-1-methyl-2(1H)-quinolinone (IV) in a mixture of 50 ml of tetrahydrofuran and 10 ml of N,N-dimethylformamide at room temperature.

After the addition is over, the reaction mixture is stirred at room temperature for an additional hour when a clear solution is obtained. Dimethyl carbonate (8 ml) is added to the reaction mixture which is then heated gradually to 100° C. and maintained there for 17 hours. The reaction mixture is cooled, filtered, and the residue is washed with ether. The solid residue is dissolved in water, acidified, and the oil is extracted with methylene chloride. Methylene chloride is stripped leaving behind an oil which is crystallized from ethylacetate to give 1.3 g of 1,2,3,4-tetrahydro-1-methyl-$\beta$,2-dioxo-6-quinolinepropanoic acid, methyl ester III, mp 175–176° C.

PREPARATION 2

1,2,3,4-Tetrahydro-$\alpha,\alpha$,1-trimethyl-$\beta$,2-dioxo-6-quinolinepropanoic acid, methyl ester (II)

To a slurry of 0.7 g of sodium hydride (60% dispersion in Nujol; 0.017 mmol) in 10 ml of N,N-dimethylformamide is added dropwise a solution of 1.3 g (0.005 mol) of 1,2,3,4-tetrahydro-1-methyl-$\beta$,2-dioxo 6-quinolinepropanoic acid, methyl ester III as prepared above in Preparation 1, in 25 ml of N,N-dimethylformamide at room temperature.

After the addition is completed, a solution of 2.8 g (0.02 mol) of iodomethane in 5 ml of N,N-dimethylformamide is added and stirring is continued for four hours. The reaction mixture is evaporated under reduced pressure and the residue is treated with water. The aqueous solution is extracted with methylene chloride. The extract is washed successively with cold 2 N sodium hydroxide solution and evaporated leaving behind 1.1 g of a viscous gum, 1,2,3,4-tetrahydro-$\alpha,\alpha$,1-trimethyl-$\beta$,2-dioxo-6-quinolinepropanoic acid, methyl ester II which was used as such for the synthesis of 6-(4,5-dihydro-4,4-dimethyl)-5-oxo-1H-pyrazol-3-yl)-3,4-dihydro-1-methyl-2(1H)-quinolinone I in the following Example 1.

EXAMPLE 1

6-(4,5-Dihydro-4,4-dimethyl)-5-oxo-1H-pyrazol-3 yl)-3,4-dihydro-1-methyl-2(1H)-quinolinone (I)

A mixture of 1.1 g of 1,2,3,4-tetrahydro-$\alpha,\alpha$-dimethyl-$\beta$, 2-dioxo-6-quinoline propanoic acid, methyl ester (II) as prepared above in Preparation 2, and 0.5 g of 80% hydrazide hydrate in 15 ml of ethanol is heated under reflux for four hours. The reaction mixture is cooled, filtered, washed with small volume of cold ethanol, and air dried to give 0.7 g of the product 6-(4,5-dihydro-4,4-dimethyl)-5-oxo-1H-pyrazol-3-yl)-3,4-dihydro-1-methyl-2(1H)-quinolinone (I), mp 235–236° C.

Anal. calcd. for $C_{15}H_{17}N_3O_2$;
Found: C, 66.40; H, 6.32; N, 15.49;
C, 66.39; H, 6.38; N, 15.31.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and moderate changes in blood pressure. This test procedure is described in the following paragraphs.

Test for In Vivo Myocardial Inotropic Activity in Anesthetized Dog

This screen consists of determining the effects of increasing intravenous doses of compound on myocardial contractility (dP/dt max of left ventricular blood pressure), heart rate, aortic blood pressure, and vascular resistance of the pentobarbital-anesthetized dog.

Methods

Adult mongrel dogs of either sex are anesthetized with pentobarbital, 35 mg/kg, IV, and are subsequently maintained under anesthesia with a continuous infusion of pentobartbal, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricle blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. Changes in vascular resistance is also recorded showing increased resistance as a peripheral effect. A period of at least 30 minutes is utilized to obtain control data prior to administration of test compound.

Depending on solubility, the compounds are dissolved in 0.9% saline solution or in dilute HCl or NaOH (0.1 or 1.0 N) and are diluted to volume with normal saline. Ethanol of dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.01 to 0.31 mg/kg/min cause dose related significant increases in cardiac contractility with only low or minimal changes in heart, moderate changes in blood pressure and increases in vascular resistance.

| | Test Results of 6-(4,5-dihydro-4,4-dimethyl)-5-oxo-1H—pyrazol-3-yl)-3,4-dihydro-1-methyl-2-(1H)—quinolinone Using Anesthesized Dog Procedure | | | | | | | | | | | |
|---|---|---|---|---|---|---|---|---|---|---|---|---|
| | Heart Rate | | | Blood Pressure | | | Contractility dP/dT max. | | | Resistance | | |
| Dose mg/kg | Beats/ Min. | % Δ | Peak Min. | mm Hg | % Δ | Peak Min. | mm Hg/ Sec. | % Δ | Peak Min. | mm Hg/ml/ min | % Δ | Peak min. |
| 0.0 | 164 | | | 175/140 | | | 3021 | | | 244 | | |
| 0.01 | 164/167 | 2 | 10 | 175/140 | 0/1 | 1 | 3021/3318 | 10 | 1 | 2.44/2.93 | 20 | 1 |
| 0.03 | 169/179 | 9 | 2 | 175/142 175/142 | −1/1 | 1 | 3083/4226 | 40 | 1 | 3.08/3.04 | 25 | 1 |
| 0.1 | 184/200 | 22 | 1 | 174/142 171/141 | −2/0 | 4 | 3655/5627 | 86 | 1 | 3.25/2.82 | 16 | 1 |
| 0.3 | 191/227 | 38 | 1 | 171/140 170/141 | −3/−4 | 9 | 4179/9478 | 214 | 1 | 3.06/2.63 | 8 | 1 |

-continued

Test Results of 6-(4,5-dihydro-4,4-dimethyl)-5-oxo-1H—pyrazol-3-yl)-3,4-dihydro-1-methyl-2-(1H)—quinolinone Using Anesthesized Dog Procedure

| Dose mg/kg | Heart Rate | | | Blood Pressure | | | Contractility dP/dT max. | | | Resistance | | |
|---|---|---|---|---|---|---|---|---|---|---|---|---|
| | Beats/ Min. | % Δ | Peak Min. | mm Hg | % Δ | Peak Min. | mm Hg/ Sec. | % Δ | Peak Min. | mm Hg/ml/ min | % Δ | Peak min. |
| 1.0 | OFF SCALE | | | 169/135 | | | | | | | | |

Accordingly, the present invention also includes a pharmaceutical composition for increasing cardiac contractility and/or treating hypertension comprising an effective amount of a compound of the formula I as defined above together with a pharmaceutically acceptable carrier.

The present invention further includes a method for incresing cardiac contractility and/or treating hypertension in mammals suffering therefrom comprising administering to such mammals either orally or parenterally a corresponding pharmaceutical composition containing a compound of the formula I as defined above in appropriate unit dosage form.

The usefulness of the compounds of the present invention as antithrombotic agents is demonstrated by their effectiveness in inhibiting human platelet aggregration in standard in vitro platelet aggregation test using human platelet-rich plasma.

Source of Platelets

Blood is collected from volunteers who have not injested aspirin or other nonsteroidal antiinflammatory drugs within the preceding two weeks and have not eaten within nine hours before blood draw. Blood is collected in 4.5 ml portions in Vacutainer Number 6462S silicone-coated tubes containing 0.5 ml of 3.8% trisodium citrate. Usually six portions of 4.5 ml are drawn from each volunteer. The blood collected from three or four volunteers is pooled prior to centrifugation. The pooled blood is put in 50 ml polyethylene tubes and centrifuged at 80 xg (ca 600 rpm) in an International Model K centrifuge with number 240 rotor for 20 minutes at room temperature. A portion (approximately two-thirds) of the supernatant platelet-rich plasma (PRP) is removed and set aside, and the remaining blood sample is recentrifuged at 1400 xg (ca 2800 rpm) for 15 minutes to prepare platelet-poor plasma (PPP). The platelet content of the PRP is determined with a Coulter Thrombocounter. The PRP is adjusted to a count of 250,000 platelets per microliter using the PPP.

Preparation of Drug Solutions

Test drugs are dissolved in small amounts of dimethyl sulfoxide (DMSO) followed by dilution with saline (final concentration of DMSO is 1%). Other lower concentrations are prepared by serial dilution in saline.

Technique of Aggregation Measurement

Platelet-rich plasma adjusted to 250,000 platelets per microliter is distributed in 0.36 ml aliquots into silicone-coated cuvettes of 0.312 inch diameter. Addition of drug solution or saline (0.02 ml) is followed by addition of aggregating agents (ADP or collagen suspension, 0.02 ml). Extent of aggregation (ADP stimulus) or rate of aggregation (collagen stimulus) is determined using the Payton Scientific Dual Channel Aggregation Module, Model 300B. Appropriate concentrations of aggregating agents are determined by an initial brief titration.

Calculations

ADP-Induced Aggregation

The height in millimeters of aggregation curves for control (no drug addition, saline only) aggregations are compared with the heights of curves obtained after drug addition at various appropriate concentrations. Heights after drug addition are finally expressed as "percent of control" values. These values are plotted versus drug concentration on semilog paper. Estimates of $IC_{50}$ values can then be made from the resulting curves.

Collagen-Induced Aggregation

The major slopes (i.e., the slope of the longest straight line portion) of collagen-induced aggregation curves are determined and compared to the slopes obtained for control aggregation curves (saline and aggregating agent only added). Values obtained are expressed as "percent of control" values. These values are plotted versus drug concentration on semilog paper. Estimates of $IC_{50}$ values are made from the resulting curves.

When tested by the above procedure, 6-(4,5-dihydro-4,4-dimethyl)-5-oxo-1H-pyrazol-3-yl)-3,4-dihydro-1-methyl-2(1H)-quinolinone had a very potent $IC_{50}$ of $3.5 \times 10^{-7}$ M against collagen-induced aggregation and had an $IC_{50}$ of $4.5 \times 10^{-6}$ M against ADP-stimulated aggregation.

Accordingly, the present invention also includes a method for treating thrombosis in mammals suffering therefrom comprising administering to such mammals either orally or parenterally a corresponding pharmaceutical composition containing a compound of the formula I as defined above in "Appropriate Unit Dosage Form."

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" in intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after convension to liquid form, multiple individual liquid doses may be obtained by measuring predetermined volume of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 10 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is ordinarily from 0.01 to 10 mg/kg of body weight per day or preferably 0.1 to 5 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

FORMULAE

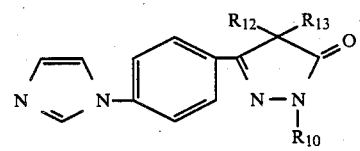

XXX

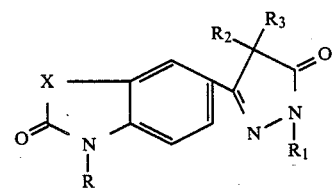

I

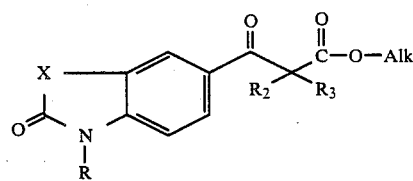

II

FORMULAE
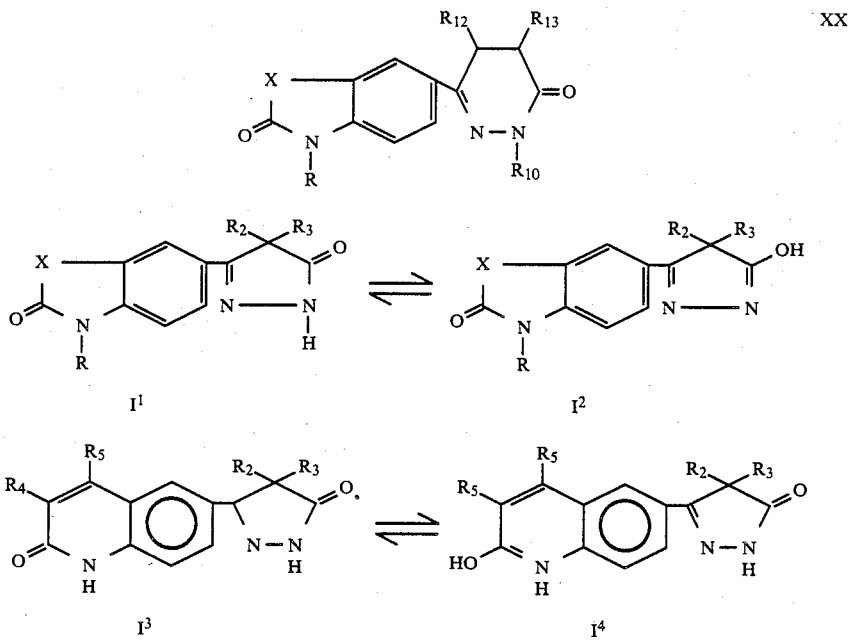
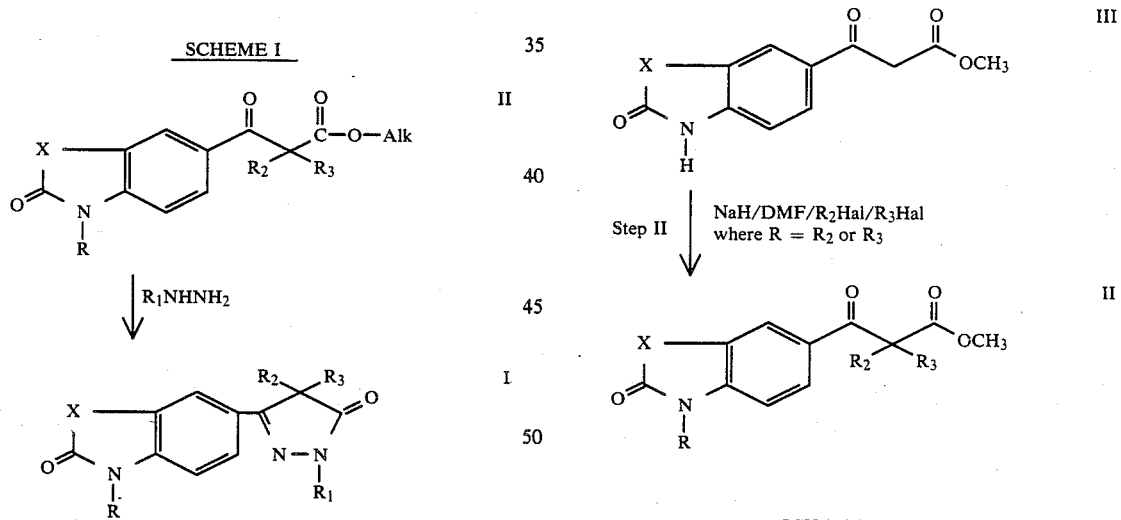
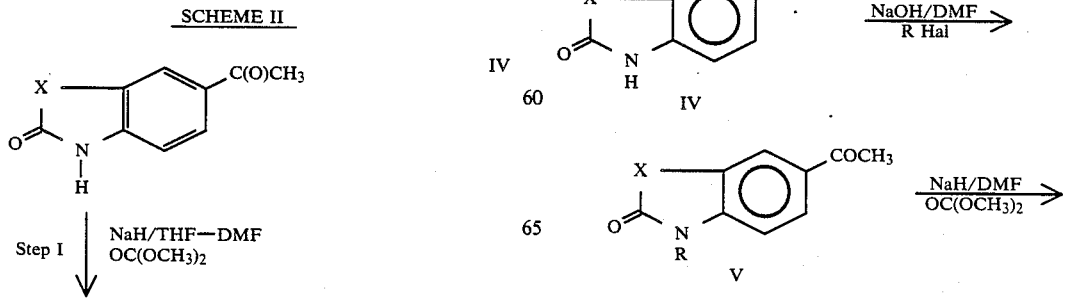

-continued
SCHEME III

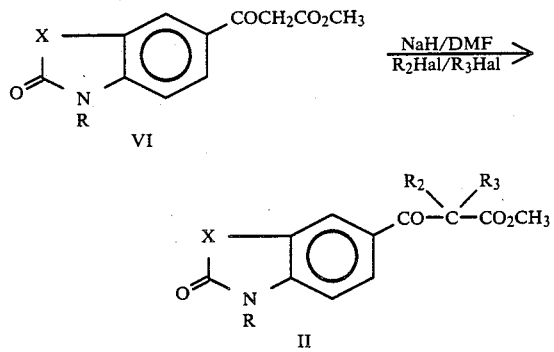

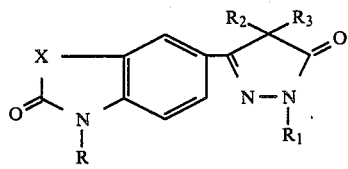

I claim:
1. A compound having the formula

I wherein X is $(CH_2)_n$ wherein n is 1 or 2, or $CR_4=CR_5$ wherein $R_4$ and $R_5$ are independently hydrogen or lower alkyl; R and $R_1$ are independently hydrogen or lower alkyl; $R_2$ and $R_3$ are independently lower alkyl or $R_2$ and $R_3$ are taken together with the carbon to which each is attached to form a ring having three to six carbons, inclusive.

2. A compound of claim 1 wherein X is $(CH_2)_2$.

3. A compound of claim 1 wherein R, $R_2$, and $R_3$ are methyl and $R_1$ is hydrogen.

4. A compound of claim 1 wherein the specific embodiment is 6-(4,5-dihydro-4,4-dimethyl-5-oxo-1H-pyrazol-3-yl)-3,4-dihydro-1-methyl-2(1H)-quinolinone.

5. A pharmaceutical composition for treatment of congestive heart failure, hypertension, or thrombosis comprising a cardiotonic, antihypertensive, or antithrombotic effective amount of a compound as claimed in claim 1 in admixture with a pharmaceutically acceptable carrier.

6. A method for increasing cardiac contractility, in a patient requiring such treatment, which comprises administering an effective amount of a pharmaceutical composition according to claim 5.

7. A method for lowering blood pressure in a patient requiring such treatment, which comprises administering an effective amount of a pharmaceutical composition according to claim 5.

8. A method for decreasing platelet aggregation in a patient requiring such treatment which comprises administering an amount of a pharmaceutical composition according to claim 5.

* * * * *